United States Patent [19]
Sandham et al.

[11] Patent Number: 4,883,534
[45] Date of Patent: * Nov. 28, 1989

[54] BENZOIN ANTIMICROBIAL DENTAL VARNISHES

[75] Inventors: H. J. Sandham, Thornhill; Thomas E. Balanyk, Toronto, both of Canada

[73] Assignee: University of Toronto Innovations Foundations, Toronto, Ontario, Canada

[*] Notice: The portion of the term of this patent subsequent to Jan. 29, 2002 has been disclaimed.

[21] Appl. No.: 63,735

[22] Filed: Jun. 18, 1987

Related U.S. Application Data

[63] Continuation of Ser. No. 680,936, Dec. 12, 1984, abandoned, which is a continuation-in-part of Ser. No. 493,755, May 11, 1983, Pat. No. 4,496,322.

[51] Int. Cl.$^4$ .................... A61K 6/00; A61K 7/16; A61K 9/08
[52] U.S. Cl. .................... 106/35; 106/15.05; 106/16; 106/208; 106/237; 424/49; 424/52; 424/407; 433/217.1; 514/900; 514/901; 523/122
[58] Field of Search ............... 433/217.1, 217; 106/35, 106/205, 208; 523/115, 122; 514/900, 901; 424/49, 52

[56] References Cited

U.S. PATENT DOCUMENTS

| | | | |
|---|---|---|---|
| 4,396,378 | 8/1983 | Orlowski et al. | 106/35 |
| 4,470,964 | 9/1984 | Chang | 424/49 |
| 4,472,373 | 9/1984 | Ryan | 424/49 |
| 4,496,322 | 1/1985 | Sandham et al. | 106/35 |
| 4,554,154 | 11/1985 | White | 426/6 |
| 4,569,837 | 2/1986 | Suzuki et al. | 514/900 |

FOREIGN PATENT DOCUMENTS 1603899 12/1981 United Kingdom .

Primary Examiner—Paul Lieberman
Assistant Examiner—Linda D. Skaling
Attorney, Agent, or Firm—Lyon & Lyon

[57] ABSTRACT

A composition for treating dental infections, e.g. dental caries caused by *Strep. mutans*, comprises a varnish containing a dentally acceptable antimicrobial agent such as chlorhexidine acetate and benzoin gum in an orally acceptable liquid. The composition can be painted on teeth, allowed to dry thereon to give a transparent, translucent or tooth colored film which is effectively invisible but provides sustained release of the antimicrobial agent to the site of infection over a period of at least four days. The film can be removed at will, e.g. by application of the liquid varnish base.

To sustain further the antimicrobial agent in situ and hinder its egress into the oral cavity, a sealing composition may be applied over the varnish layer. The sealing composition is preferably solvated polyurethane which cures by evaporation of solvent.

11 Claims, 3 Drawing Sheets

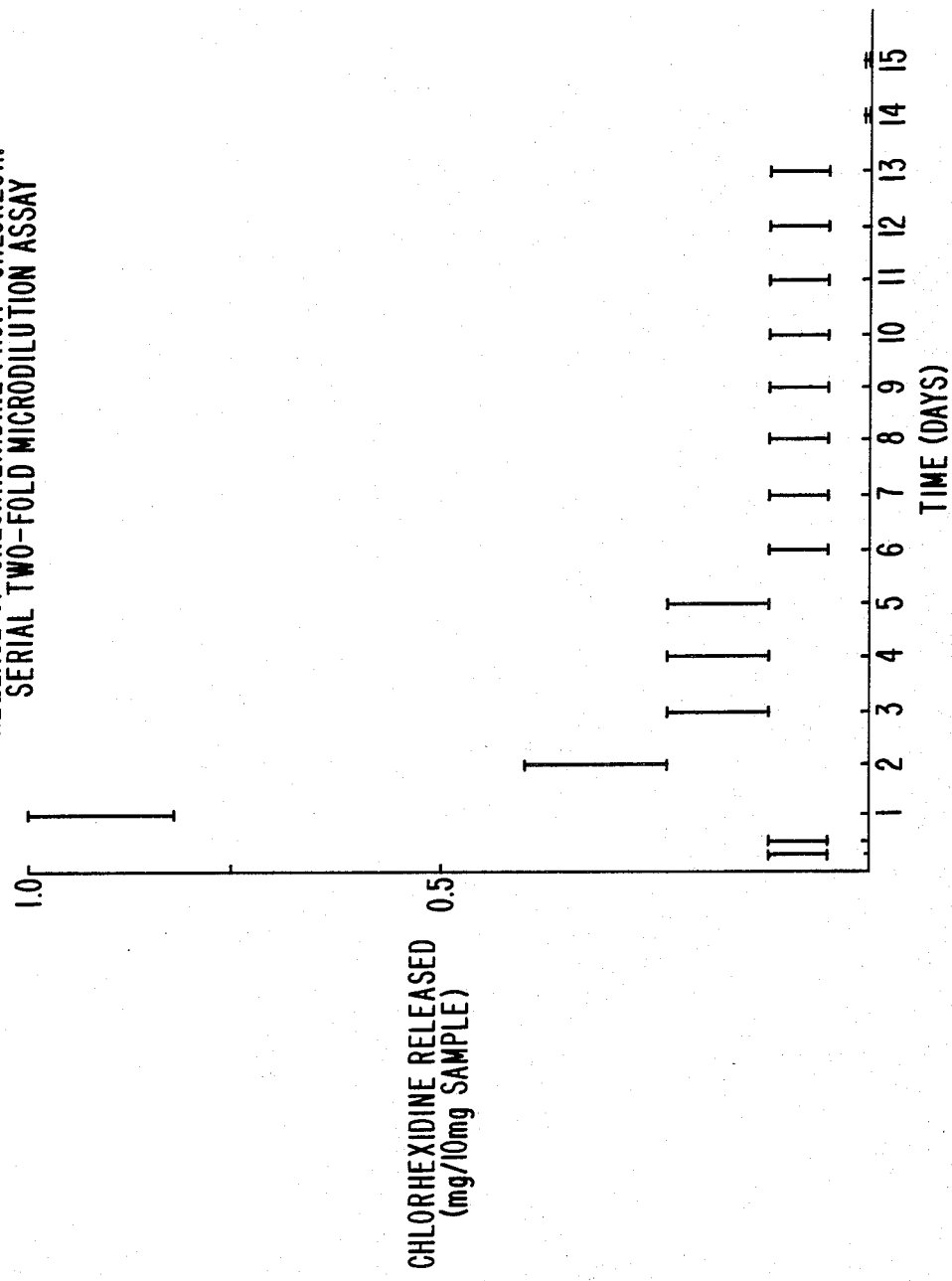

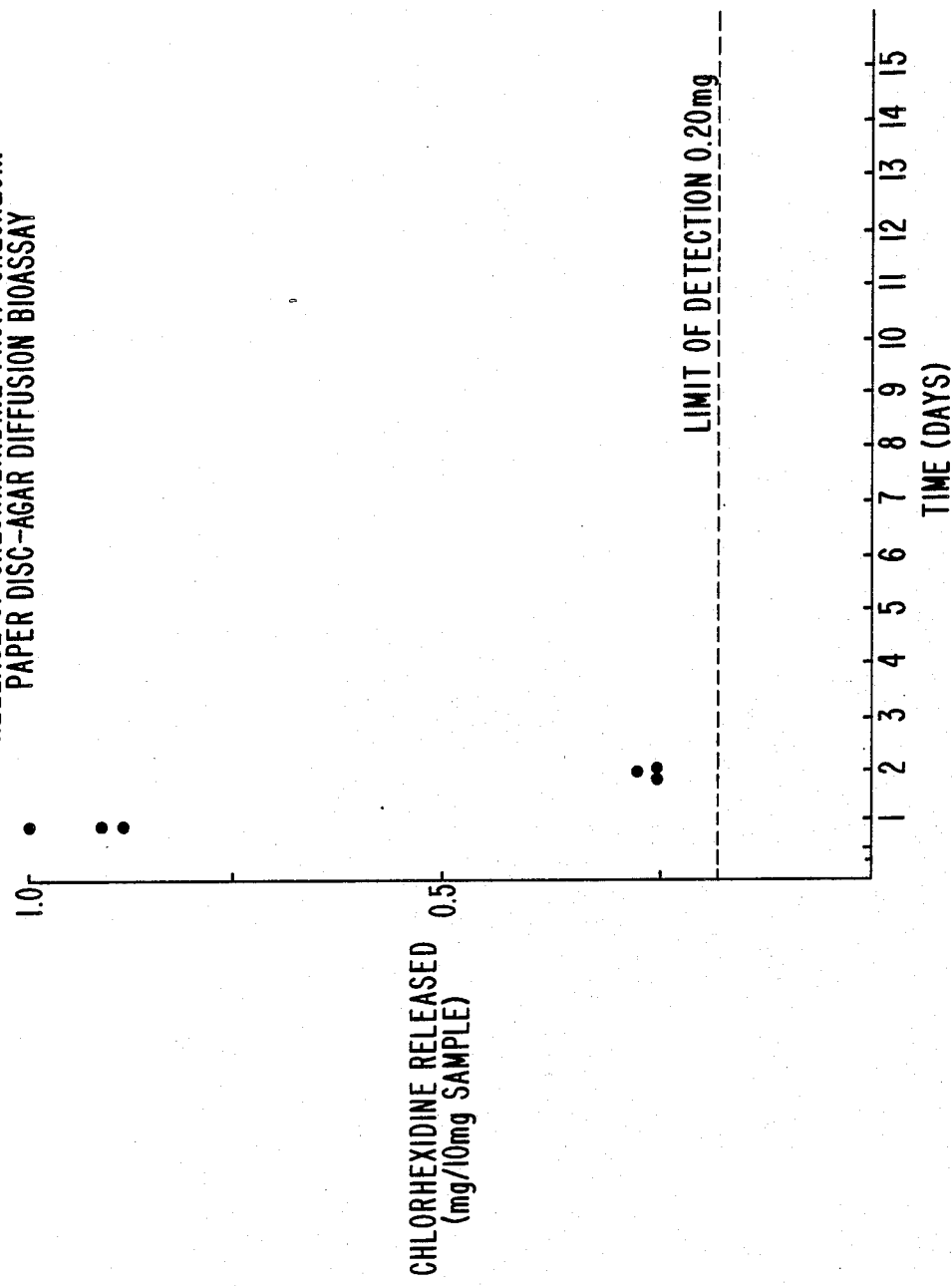

BENZOIN ANTIMICROBIAL DENTAL VARNISHES

RELATED APPLICATION

This application is a continuation of application Ser. No. 680,936, filed 12/12/84, now abandoned, which is a continuation-in-part of application Ser. No. 493,755 filed May 11, 1983 now abandoned.

FIELD OF THE INVENTION

The present invention relates to compositions and methods for treatment and prevention of oral infections.

BACKGROUND

Evidence is accumulating which indicates that both dental caries and periodontal disease may result from infection by specific components of the oral microflora. Elimination of these infections should therefore contribute to treatment and prevention of these disorders.

It is known to apply antiseptics topically to teeth, gums etc. as mouthwashes and in gels. Systemic administration of antibiotics is sometimes prescribed for treatment of periodontal disease. While both such methods are effective in reducing oral bacterial counts, the active ingredients seldom remain at the site of infection in effective concentration for a time long enough for fully effective treatment. Topically applied liquid antiseptics such as mouthwashes are easily washed from the infection site by salivation and routine mastication.

A properly effective, convenient and patient-acceptable means for effecting treatment of dental infections, such as dental caries caused by *Strep. mutans* infections, has not heretofore been developed. Such a means needs to be effective to contact the site of infection with the antimicrobial treating agent over an extended period of time, for example several days. Moreover, it should be capable of effecting treatment without the over-frequent or continuous adjustments, modifications, inspections and monitorings requiring professional attention. It must of course resist premature removal from the infected site as a result of normal salivation, mastication and intake of food and beverage. Finally, but equally importantly, it must be acceptable to the patient, in terms of its taste, external appearance, texture, effect on oral sensitivities, odour, and freedom from interference with normal oral functions.

BRIEF REFERENCE TO THE PRIOR ART

It is also known to use a composition consisting of compound benzoin tincture binder, benzocaine and cetylpyridium chloride with other ingredients, for oral topical application for treatment of canker sores (Blistex Incorporated, "Kank-A"). Such a composition is not, however, suitable for application to teeth to treat or prevent dental caries. Firstly, the formulation contains ingredients which impart an unpleasant, bitter taste thereto, so that it is not acceptable for use in applications where it will be retained in the oral cavity for extended periods of time. Secondly, it imparts discoloration to teeth when applied thereto. Thirdly, it contains toxic ingredients.

SUMMARY OF THE INVENTION

It is an object of the present invention to provide an oral composition effective for combatting growth of infection causing bacteria and capable of adherence to the infection site, and retention in the oral cavity.

It is a further object of the present invention to provide a novel, orally acceptable composition which has acceptable taste and color characteristics to permit its use on patients' teeth for periods of time necessary to effect treatment of dental caries infection.

It is a further object of the present invention to provide a two component kit, a first component of which has acceptable taste, colour and antimicrobial characteristics to permit its use on patients's teeth and which remains on the teeth for a period of time sufficient to effect treatment of oral infection and a second dentally acceptable component of which is effective to sustain the first component in situ.

It is a further object of the invention to provide a method of combatting and treating oral infections.

In a first aspect of the present invention, a composition suitable for dental use and effective in combatting growth of disease causing bacteria is provided, the composition comprising at least one dentally acceptable antimicrobial agent, and a dentally and biologically acceptable binder material. The composition as a whole can be adhered to the site of dental infection. The binder material is capable of permitting effective communication of said antimicrobial agent with the infection site when the composition is applied thereto, over an extended period of time, to effect treatment. The residue of the composition after treatment is readily removed at will.

In a second aspect of the present invention there is provided a two component kit, the ingredients of which are capable collectively of combatting growth of disease causing bacteria indigenous to the oral cavity. This embodiment entails provision of a sealing composition for application over the composition bearing the antimicrobial agent in order to prolong availabilty of the agent to the infection site.

DESCRIPTION OF THE PREFERRED EMBODIMENTS

The antimicrobial-varnish composition may initially be prepared in any form suitable for application to teeth or gingiva, in the oral cavity, such as pastes, liquids, semi-solids or the like, provided that the binder and anitmicrobial agent adhere to the structures to which they are applied. Suitably, the composition is initially prepared in the form of a liquid varnish, in an appropriate solvent, and applied to oral structures as such. After application, the solvent evaporates to leave a solid deposit, film or coating on the structure to which it has been applied. The solid consists essentially of the binder material and the antimicrobial agent or agents. The binder material permits a slow release of the antimicrobial agent or agents to the applied site, for prolonged treatment of the site therewith.

A specific preferred binder material is benzoin gum, either Sumatra or Siam benzoin, or fractions or recombined fractions thereof (hereinafter referred to as benzoin for brevity), which is capable of adherence to the tissues and enamel of the gingiva and teeth respectively. The benzoin is soluble in ethanol, which constitutes a suitable solvent to make the varnish composition, and is also compatible with several suitable antimicrobial drugs. After application to the infected site, a composition formed from the benzoin, ethanol and antimicrobial agent dries to form a solid, permitting a sustained release of the active antimicrobial ingredient over an extended period of time. Repeated applications of antimicrobial-varnish compositions of the present invention are not required on a frequent basis, for effective treatment. It has been found that the antimicrobial agent is effectively maintained at the infection site for at least four days owing to the presence of the benzoin film. The composition can be removed at will, by application of the appropiate solvent, normally ethanol, to the solid or by other standard oral hygiene techniques.

Preferred antimicrobial-varnish compositions according to the present invention include a plurality of antimicrobial agents.

A wide variety of dentally acceptable antimicrobial agents can be used in compositions according to this aspect of the invention, choice among which is determined largely on the basis of the infection which it is required to combat and safety to the patient. Erythromycin and chlorhexidine are examples of suitable preferred agents for combatting common oral bacterial infections.

Chlorhexidine is preferably used in the form of an orally acceptable salt thereof, e.g. acetate, hydrochloride or gluconate. Most preferred among chlorhexidine salts is chlorhexidine acetate on account of its appropriate solubility in water and in the preferred solvent ethanol, to provide good rate of release from the film.

The relative proportions of binder, antimicrobial agents and solvent in the preferred antimicrobial-varnish composition can vary widely. The lower solvent limit is fixed only by the maximum solubility of the other ingredients therein. The ratio of antimicrobial agent to solvent can be anywhere from 0.001% w/v up to a saturated solution thereof, e.g 20%. The ratio of antimicrobial agent to binder is suitably in the range 10:1 to 1:10 by weight, preferably 5:1 to 1:5, and most preferably 2:1 to 1:2. Precise preferred ratio depends to some extent on the rate of release of the antimicrobial agent from the film. It is preferred to subject the site of infection initially to relatively large amounts of antimicrobial agent, to reduce the chance of formation of antimicrobial resistance in the infection.

Antimicrobial-varnish compositions, according to the present invention, are best formulated from only three essential ingredients, namely the benzoin binder, the ethanol solvent, and the antimicrobial agent or agents. Such a composition contains only orally acceptable, nontoxic ingredients. It contains no ingredients likely to have the effect of discoloring the dental site to which it is applied. With choice of the most appropriate antimicrobial agents, the hardened film contains no ingredients imparting thereto an unacceptable taste or texture, rendering it unpleasant to the user. It is suitably and conveniently applied by painting onto the site of infection. It adheres strongly to the teeth or gums, and penetrates effectively into fissures and pits on the tooth surface. After application to the teeth, the antimicrobial-varnish composition dries in a relatively short period, e.g. about 3-6 minutes to yield a strongly adherent, clear or tooth-colored film which is effectively invisible whilst in place. It is strong enough to remain on the teeth for an extended period of time, at least four days, and will resist the forces commonly applied during mastication. Whilst the film is in place, of course, the user must refrain from application thereto, of the solvent ethanol as part of the user's drink intake, but the film can nevertheless be removed as and when required, at will, by simple application thereto of ethanol solvent and employment of standard oral hygiene procedures.

Whilst in place, the film releases the antimicrobial agent or agents contained therein at a slow, relatively constant rate, and in concentration sufficient effectively to combat the target bacteria over a period of several days. Finally, the solvent used, namely ethanol, is compatible with restorations present in the teeth as well as original tooth enamel and does not dissolve or soften them. If desired, the antimicrobial varnish composition may additionally include small amounts of additional ingredients such as flavorants or flavor maskers, texturizers or other tooth treating aids such as fluorides.

In addition to application to teeth, gingiva etc. by painting thereon as a liquid, dryable varnish, one can also apply antimicrobial-varnish compositions of the invention as pastes, e.g. in a toothpaste formulation, as a liquid mouthwash, as a chewable tablet or the like, as long as an adherent film of binder and antimicrobial agent is applied in a semi-permanent manner to the site of infection, e.g., at least overnight.

The antimicrobial varnish composition, which constitutes a first aspect of the present invention, has been found to maintain a concentration of antimicrobial agent on the target site which is adequate for treatment of oral bacterial infection, including colonization of *S. mutans* which is believed responsible for dental caries. According to a second aspect of the present invention, the efficacy of the antimicrobial varnish formulation may be augmented by application of a sealing layer over the antimicrobial-varnish layer. The addition of the sealing layer acts to hinder egress of antimicrobial agent from the varnish composition into the saliva and oral cavity, thus sustaining a greater concentration of the active agent in situ for effective treatment.

The sealing layer is necessarily comprised of ingredients which meet the criteria required of the antimicrobial varnish layer, i.e. dental acceptance in terms of colour, toxicity and taste as well as compatibility with amalgams and tooth enamel and, of course, compatibility with the varnish layer discussed above.

It has been found that polymeric films are suitable as sealants for the purpose of this embodiment of the present invention. Selection of appropriate such polymeric films is appropriately based on the criteria mentioned hereinbefore together with the requirement that the polymer employed is able to be deposited from a dentally acceptable solvent, thus allowing the film to be applied easily in liquid form and later curing to deposit the desired sealing layer. Suitable such films include those formed from polyurethanes and polylactates.

In view of the fact that the liquid sealant is able to penetrate crevices and fissures of the teeth and will cure in situ, the polymer sealant should be biodegradable so as conveniently not to remain for excessive periods in areas which are not easily accessible.

Preferred sealants include polyurethane varnishes (polyurethane in suitable solvent such as methylene chloride) which contain fluoride, such as, for example, the composition known as FLUOR-PROTECTOR ®, a fluoride-containing polyurethane varnish manufactured by Ivoclar-Vivadent employing methylene chloride as the solvent, ADHESIT ® and PLUS-PROTECTOR ®, compositions similar to FLUOR-PROTECTOR ® and manufactured by the same company but lacking the fluoride component, and in some instances using ethanol or Freon as solvents. Inclusion of the fluoride component is most preferred in view of the evidence supporting efficacy of fluoride in combatting loss of tooth mineral.

Application of the sealant is conducted after the antimicrobial varnish layer has been applied and allowed to dry. The sealant is applied in liquid form, i.e. in solution with a suitable solvent, e.g. by painting, over the entire area contained by the antimicrobial varnish layer. The fluid condition of the uncured sealant allows the sealant to infiltrate fissures and crevices and other tooth surfaces bearing the antimicrobial agent and to seal the antimicrobial agent in a position effective to maintain communication of the agent with the target site and hinder its egress into the oral cavity. Once applied, the sealant is allowed to cure by evaporation of solvent to form a hard transparent or translucent film over the varnish layer.

Drying of the sealing layer is generally instantaneous, but may be assisted, if necessary, by an air syringe of the type typically employed by a dentist.

The resident time of the sealing layer over the application site is normally at least four days, a period of time which parallels the resident time of the antimicrobial-varnish layer. Thus, re-application of the varnish layer and sealing layer may normally be effected at the same time, as required. Also, presence of the sealing layer over the antimicrobial-varnish layer effectively removes the requirement that the user refrain from ethanol intake since the sealing layer is not soluble therein.

BRIEF DESCRIPTION OF THE DRAWINGS

FIGS. 1, 2 and 3 are graphical representation of the results of experiments reported in Example 4.

Figure 1:
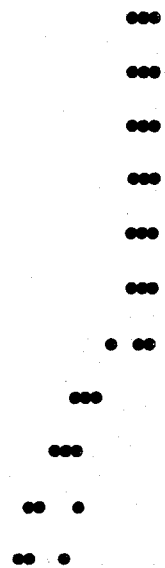

The invention is further described in the following specific, nonlimiting examples:

EXAMPLE 1

Varnish Formulation containing antimicrobial agent

A formulation according to the invention was made by dissolving 1 gm chlorhexidine acetate in 10 ml of tincture of benzoin, which consisted of a 10% w/v solution of Sumatra benzoin in 95% ethanol, (hereinafter referred to as "CHLORZOIN"* formulation). A similar formulation was prepared using erythromycin in place of chlorhexidine (to form an "ERYTHROZOIN"* formulation). These liquid formulations were then used as varnishes, to paint and coat oral structures for a temporary period, as described in the subsequent examples.

*Trademark to be applied for

EXAMPLE 2

Extracted molars, with clear fissures and containing neither visible caries nor amalgams, were provided. The apical foramen of each tooth was sealed with methyl-2-cyanoacrylate and then the teeth were dried for 24 hours at 22° C. The teeth were then placed in 95% ethanol for 24 hours and dried for four hours at 37° C. in covered sterile petri dishes.

Each molar was placed in a tube containing a 20 ml solution of Todd Hewitt broth (THB) and 5% sucrose. Nine tubes were inoculated with 0.1 ml of JC2 strain of S. mutans ($10^8$/ml in tryptic soy) and another nine molar-containing tubes were inoculated with a 0.1 ml of a mixture of S. mutans (comprised of E-49, BHT, JC2, PS-14, PS-72, 01H1, 6715, PK1, LM7 and ATCC 10499) of varying concentrations.

The molar and broth-containing tubes were incubated for 72 hours in a 90% $N_2$, 10% $CO_2$ atmosphere in standard incubating jars at 37° C. whereafter the teeth were removed and aseptically transferred to covered sterile petri dishes where they were dried for 2 hours in a warm room (37° C.).

Nine teeth grown in broth containing only the JC2 strain were painted with 0.1 ml of different varnishes prepared according to Example 1. The first group of three was painted with tincture of benzoin. The second group was painted with CHLORZOIN. ERYTHROZOIN was painted on the teeth forming group three.

A similar test was performed on nine teeth incubated with the multi-strain inoculated tubes.

The painting was performed with FLUOR-PROTECTOR® disposable brushes manufactured by Ivoclar-Vivadent. The brushes were gas sterilized before use.

After application of the varnish, the coated teeth were dried on covered sterile petri dishes for 30 minutes at 37° C.

All teeth were then placed in 100 ml THB (5% sucrose) solution for 24 hours at 37° C. under 90% $N_2$ and 10% $CO_2$ atmosphere.

The varnishes were then removed with rotating bristle brushes in a slow speed dental handpiece.

To analyze bacterial growth, each tooth was placed in 100 ml of Shklair's medium at 37° C. for 14 days (90% $N_2$ and 10% $CO_2$ added). The results are shown in Table I. Bacterial growth is indicated by a change of medium colour from purple to yellow, indicated by "+" in the table below which summarized the results of the procedure supra.

TABLE I

| Varnish + JC2 | | | | Varnish + mixture | | | |
|---|---|---|---|---|---|---|---|
| Tooth | Benzoin | CZ | EZ | Tooth | BZ | CZ | EZ |
| 1 | + | | | 10 | + | | |
| 2 | + | | | 11 | + | | |
| 3 | + | | | 12 | + | | |
| 4 | | − | | 13 | | − | |
| 5 | | − | | 14 | | − | |
| 6 | | − | | 15 | | − | |
| 7 | | | − | 16 | | | − |
| 8 | | | − | 17 | | | − |
| 9 | | | − | 18 | | | − |

"+" indicates a color change, and
"−" indicates no color change, after fourteen days Table 1 indicates the efficacy of the CHLORZOIN and ERYTHROZOIN varnishes in inhibiting growth of S. mutans strains in vitro.

EXAMPLE 3

In vivo testing of tincture of benzoin and of CHLORZOIN.

An in vivo trial was undertaken using tincture of benzoin, both with and without chlorhexidine, as described in Example I in the mouth of one of the investigators. The handling and other properties of the preparations were found to be as satisfactory as in vitro properties. The film formed on the teeth in vivo closely resembled that formed in vitro. Additionally, the taste of the tincture of benzoin, although balsamic, was not objectionable to the patient. However, when CHLORZOIN was applied, its taste was objectionable. The taste became acceptable, however, when the teeth were first isolated from one another and dried using cotton roll prior to application of the CHLORZOIN. The cotton rolls were left in place until after the CHLORZOIN had hardened (a few minutes).

EXAMPLE 4

KINETICS OF RELEASE OF CHLORHEXIDINE FROM FILMS OF "CHLORZOIN"

The purpose of using varnish as a vehicle for delivering chlorhexidine was to release low levels of chlorhexidine slowly over a period of days in the vicinity of the tooth surface, the only site of S. mutans colonization in the mouth.

As an aid for predicting the rate of release of chlorhexidine from CHLORZOIN in the oral cavity, in vitro experiments in which solidified films of CHLORZOIN, of standardized weight (10 mg chlorhexidine and 10 mg of benzoin) and shape, were utilized. The lens-shaped films were prepared by pipetting 0.1 ml of CHLORZOIN into standardized moulds, and permitting them to dry in the air. The films were then placed in 10 ml of TRIS buffer for 15 days. The buffer solutions were constantly agitated and were completely replaced after 6, 12, and 24 hours and daily thereafter.

The removed buffer solutions were then assessed for their cholorhexidine content by three methods that were, in preliminary experiments, found to provide reproducible assessments of chlorhexidine concentration. The methods were (i) UV absorption at 256 nm, (ii) serial two-fold microdilution (Little et al., 1979), and (iii) paper disc-agar diffusion (Barry, 1981). The last two methods are biological assays, utilising antimicrobial effectiveness to estimate chlorhexidine concentration.

The results are presented graphically in appended FIGS. 1, 2 and 3, derived from triplicate test samples. They show chlorhexidine release for each time interval from 0.02 g of dried CHLORZOIN film. Following a slow initial release of chlorhexidine for the first 12 hours, there was an almost 10-fold greater release during the second 12 hour period. However, by the end of the third day, chlorhexidine release had decreased to approximately 0.1 mg per sample per day. Thereafter, it maintained an almost constant rate of release until approximately the 11th day, when the release rate began to fall off to zero by 14 days.

From these results it may be concluded that CHLORZOIN is capable of releasing chlorhexidine at a low rate over a period of several days, consistent with its use for eliminating S. mutans from the human oral cavity. The concentration of chlorhexidine attained in each sample of buffer solution during the period of slow release (approximately days 3 to 11) was approximately 10 ug/ml, a concentration which is known to be bactericidal in vitro for S. mutans. Thus, the concentration of chlorhexidine released during the slow release period seems potentially adequate to kill S. mutans in the immediate vicinity of the teeth.

The above data can also be used to provide a rough estimate of the maximum dose to a patient over a 24 hour period. The amount of CHLORZOIN required to coat the teeth of an adult subject with a complete natural dentition was found to be approximately 1.5 ml, approximately 15 times greater than that in each sample in these in vitro experiments. The results reported here (FIGS. 1, 2 and 3) indicate that approximately 1.2 mg of chlorhexidine was released in vitro over the first 24 hours, the period of maximum release. If the release rate were assumed to be similar in the human mouth, a human might be expected to ingest a maximum of approximately 18 mg of chlorhexidine (1.2 mg×15) over a 24 hour period. This amount is well below that generally recognized as safe in humans.

The embodiment of the invention in which a sealing layer is applied over the antimicrobial varnish layer of the type exemplified in Examples 1 to 4 is hereinafter illustrated in specific non-limiting examples:

EXAMPLE 5

Formulation of antimicrobial varnish

Additional formulations were prepared according to the procedure outlined in example 1 to provide the test formulations listed in Tables 2 and 3, below:

TABLE 2

| Amount of Chlorhexidine Acetate (weight % of composition) | Amount of Benzoin (weight % of composition) | Abbreviated Name |
|---|---|---|
| 20 | 40 | Chlor 20-40 |
| 10 | 10 | Chlor 10-10 |
| 20 | 10 | Chlor 10-20 |

Similar ERYTHROZOIN* formulations were prepared in a similar manner by substituting erythromycin for chlorhexidine acetate in varying amounts as listed in Table 3 below:

TABLE 3

| Amount of Erythromycin (weight % of composition) | Amount of Benzoin (weight % of composition) | Abbreviated Name |
|---|---|---|
| 10 | 20 | Ery 10-20 |
| 10 | 10 | Ery 10-10 |

In all of the above formulations (Tables 2 and 3) the balance of the composition was 95% ethanol.

EXAMPLE 6

Sealant

To examine and compare the utility of various sealing compositions, the following compositions were employed. In vitro and clinical data generated by their use apppear in subsequent examples:

| Sealant | Composition |
|---|---|
| (1) Benzoin (SB) | 20% benzoin in ethanol |
| (2) PLUS PROTECTOR ® (Ivoclar-Vivadent) | polyurethane dissolved in methylene chloride |
| (3) ADHESIT ® (Ivoclar-Vivadent) | non-fluoride containing polyurethane varnish in |
| (4) FLUOR-PROTECTOR ® (Ivoclar-Vivadent) | fluoride-containing polyurethane varnish in methylene chloride |
| (5) PFE | polyurethane dissolved in a mixture of 65% Freon and 35% ethanol |

Note: PLUS-PROTECTOR ® and ADHESIT ® are similar formulations. ADHESIT ® contains a more selective molecular weight range of polymer than does PLUS-PROTECTOR ®.

EXAMPLE 7

In vitro study of effects of various polyurethane varnishes on the slow-release properties of CHLORZOIN.

The experiment was performed to examine the rate of release of chlorhexidine from CHLOR 20-40 varnish (20% chlorhexidine acetate, 40% Sumatra benzoin in ethanol) when applied to a stainless steel wire (simulating the tooth). Wire pre-coated by successive dipping into CHLORZOIN with intermittent drying was placed in a 0.1M Tris HCl buffer, pH=7.0, at 37° C. simulating saliva and the concentration of chlorhexidine acetate in the buffer was subsequently measured at daily intervals by standard spectro-photomeric techniques for two days using fresh buffer each day. On the third day, the varnish and chlorhexidine acetate remaining were scraped off the wire into fresh buffer and its concentration measured to determine the amount of chlorhexidine acetate remaining in the varnish and thus available during the first two days to infiltrate fissures and crevices where S. mutans thrive.

The results generated by use of Chlor 20–40 per se were compared with results obtained when selected sealant coatings were applied over the Chlor 20–40 treated wire. These comparative results appear in Table 5 below:

TABLE 5

| Trial | Primary Coat | Sealing Coat | Chlorhexidine content of buffer (mg/ml) | | |
|---|---|---|---|---|---|
| | | | Day 1 | Day 2 | Day 3 (residue) |
| (1) | Chlor 20-40 | — | 8.8 | 12.2 | 90.2 |
| (2) | Chlor 20-40 | FLUOR-PROTECTOR ® | 0.3 | 1.8 | 192.0 |
| (3) | Chlor 20-40 | ADHESIT ® | 7.8 | 9.3 | 108.0 |

From the above results, it can be seen that while Chlor 20–40 afforded adequate sustained release of chlorhexidine, use particularly of FLUOR-PROTECTOR ® as an additional sealing coat substantially decreased release of chlorhexidine into the surrounding buffer indicating maintainence of the active ingredient in position on the target area. A greater portion of the original concentration of chlorhexidine is thus made available to the application site by use of the sealing compositions. Use of ADHESIT ® as a sealing coat also recorded desireable results. Similar experimentation indicates that the PFE composition also adequately meets the desired criteria. Thus, it is shown that application of a sealing coat of PFE, ADHESIT ® and, more preferably, of FLUOR-PROTECTOR ® over a dried layer of Chlor 20–40 provided an improved means of sustaining the active ingredient in situ when compared with the ability of Chlor 20–40 per se to accomplish the same objective.

EXAMPLE 8

Clinical Trials

Over an initial period of 17 weeks a variety of compositions were tested on two subjects (hereinafter referred to as #1 and #2) by painting specific respective compositions over their teeth. Each layer was allowed to dry before any superior layer was applied. Initially, saliva samples were taken from each mouth, plated and incubated appropriately to determine the average count of S. mutans within each mouth by standard microbiological techniques. Success or failure of the particular composition was evaluated on the basis of reduction in number of the average count of S. mutans observed in samples taken after one week of wearing the composition as compared with the count when no formulation was in use. Regardless of whether the same composition or a different composition was emplyoed, the compositions were applied or re-applied each week.

Tables 6 and 6a appearing below summarize the results obtained during the initial testing period, in which no polyurethane sealing coat was applied (SB denotes 20% benzoin sealing coat):

TABLE 6

(Subject #1)

| Week | Varnish Treatment | S mutans saliva count one week later CFU/ml) |
|---|---|---|
| 0 | — | 250,000 |
| 1 | Chlor 10-10 | 10,000 |
| 2 | Chlor 10-10 | — |
| 3 | Chlor 10-10 | 500 |
| 4 | Ery 10-20 | 10,000 |
| 5 | Ery 10-20SB | 7,000 |
| 6 | Ery 10-20SB | 4,000 |
| 7 | Chlor 10-20 | — |
| 8 | Chlor 10-20SB | 80 |
| 9 | *Pen 10-20 | 75 |
| 10 | Pen 10-20SB | plate contamination |
| 11 | — | — |
| 12 | — | — |
| 13 | — | — |
| 14 | Chlor P20-40SB | 200 |
| 15 | — | — |
| 16 | Chlor P20-40SB | 200 |
| 17 | Chlor P20-40SB | 7,500 |

*Pen 10-20 denotes 10% penicillin in 20% benzoin varnish.

TABLE 6a

SUBJECT #2

| Week | Varnish Treatment | S mutans saliva count one week later CFU/ml) |
|---|---|---|
| 1 | — | 720,000 |
| 2 | Chlor 10-10 | 10,000 |
| 3 | Chlor 10-10 | 600 |
| 4 | Ery 10-20 | 10,000 |
| 5 | Ery 10-20SB | 500 |
| 6 | Chlor 10-20SB | 0 |
| 7 | — | 600 |
| 8 | Chlor 10-20SB | 80 |
| 9 | Pen 10-20 | 500 |
| 10 | Pen 10-20SB | plate contamination |
| 11 | — | — |
| 12 | — | — |
| 13 | — | — |
| 14 | Chlor P20-40SB | 700 |
| 15 | — | — |
| 16 | Chlor P20-40SB | 2,000 |
| 17 | Ery P20-40SB | 400 |

(missing entries denote absence of testing during specified period.)

The ability of a composition to reduce the bacterial count is indicative of the ability of the composition to sustain presence of the antimicrobial agent over the application site, in cases where equal concentrations of antimicrobial agents were employed. As the tables above indicate, use of Chlor 10–10 over the first few weeks of trial reduced the S. mutans counts appreciably although the bacteria was not eliminated. Various other treatments including application of Ery 10–20, Chlor 10–20 or the same each with a sealing coat of 20% benzoin (SB) generated similar results. In all of the initial attempts, only once was S. mutans absent from the saliva test sample (week 6, Table 6a), a result which was only temporary (see Week 7, same Table).

Substantial reduction in the presence of S. mutans was achieved in the latter portion of the clinical study in which PLUS-PROTECTOR ® was employed as sealant over Chlor 20-40. This combination of layers is denoted Chlor P20-40SP in Tables 7 and 7a which summarize results obtained from Subject #1 and Subject #2, respectively:

TABLE 7
EFFECT OF VARNISH TREATMENTS ON *S. MUTANS* (SUBJECT #1)

| Week | Varnish Treatment | Salivary *S. Mutans* One Week Later (CFU/ml) | *S. Mutans*-Free Periods |
|---|---|---|---|
| 18 | Chlor P20-40SP | 0 | 2 weeks |
| 19 | — | 0 | — |
| 20 | — | 200 | — |
| 21 | Chlor P20-40SP | 0 | — |
| 22 | — | 0 | 2 weeks |
| 25 | (Intentional reinfection) | — | — |
| 27 | — | 1,000 | — |
| 29 | Chlor P20-40SP | 0 | — |
| 39 | — | 0 | — |
| 43 | — | 0 | 28 weeks |
| 48 | — | 0 | — |
| 51 | — | 0 | — |
| 53 | — | 0 | — |

TABLE 7a
EFFECT OF VARNISH TREATMENTS OF *S. MUTANS* (SUBJECT #2)

| Week | Varnish Treatment | Salivary *S. Mutans* One Week Later (CFU/ml) | *S. Mutans*-Free Periods |
|---|---|---|---|
| 18 | Chlor P20-40SP | 0 | — |
| 19 | — | 0 | 3 weeks |
| 20 | — | 0 | — |
| 21 | — (Broken cusp) | 1,500 | — |
| 22 | Chlor P20-40SP | 0 | — |
| 26 | — | 0 | 11 weeks |
| 31 | — | 0 | — |
| 33 | — | 20 | — |
| 34 | — | 1,500 | — |
| 37 | — | 7,000 | — |
| 39 | Chlor P20-40SP | — | — |
| 45 | Chlor P20-40SP | 0 | — |
| 48 | Chlor P20-4-SP | 0 | — |
| — | — | — | 4 weeks |

Although freedom from *S. mutans* is rarely found in individuals having teeth, the results tabulated above indicate the efficacy of the tested compositions in substantially or virtually eliminating the presence of the bacteria from the saliva test samples. Subject #1 exhibited at least 28 consecutive weeks of freedom from *S. mutans* colonization, even after intentional re-infection with the bacteria in week 25.

Two other test subjects, #3 and #4 were treated with Chlor P20-40SP to repeat testing of this particular composition. The results appear in Tables 7b and 7c below:

TABLE 7b
EFFECT OF VARNISH TREATMENTS ON *S. MUTANS* SUBJECT #3

| Week | Varnish Treatment | Salivary *S. Mutans* One Week Later (CFU/ml) | *S. Mutans*-Free Periods |
|---|---|---|---|
| 1 | None | 5,000,000 | — |
| 0 | Chlor P20-40SP | 100 | — |
| 1 | Chlor P20-40SP | 0 | — |
| 2 | Chlor P20-40SP | 0 | — |
| 3 | — | 0 | — |

TABLE 7b-continued
EFFECT OF VARNISH TREATMENTS ON *S. MUTANS* SUBJECT #3

| Week | Varnish Treatment | Salivary *S. Mutans* One Week Later (CFU/ml) | *S. Mutans*-Free Periods |
|---|---|---|---|
| 5 | — | 0 | 5 weeks |
| 6 | — | 4,000 | — |
| 7 | Chlor P20-40SP | 0 | — |
| 8 | — | 0 | — |
| 9 | — | 0 | — |
| 11 | — | 0 | 28 weeks |
| 31 | — | 0 | — |
| 34 | — | 0 | — |

TABLE 7c
EFFECT OF VARNISH TREATMENTS ON *S. MUTANS* SUBJECT #4

| Week | Varnish Treatment | Salivary *S. Mutans* One Week Later (CFU/ml) | *S. Mutans*-Free Periods |
|---|---|---|---|
| 0 | — | 2,000 | — |
| 1 | Chlor P20-40SP | 0 | — |
| 2 | — | 0 | — |
| 3 | — | 0 | — |
| 5 | — | 0 | 33 weeks |
| 33 | — | 0 | — |

Although the initial concentration of *S. mutans* was very high in Subject #3, application of the PLUS-PROTECTOR ® sealant over a layer of 20% chlorhexidine in 40% benzoin was able to reduce the bacterial count substantially in the first few weeks and completely eliminated the bacteria from week 7 onward. Similar favourable results were generated by Subject #4.

An important feature of the present invention is that the compositions, when applied to teeth, are not readily visible to the outside observer. The films are colorless, clear or translucent, or the same essential color as the teeth themselves. They thus are acceptable both to the dental profession and the user, as an unobtrusive and convenient aid to dental care, which will not risk causing discoloration of the teeth afterwards. Moreover, they are easily formulated so as to be quite acceptable as to taste.

While the invention has been illustrated with reference to certain specific working examples, its scope is not to be construed as limited thereby. The scope of the invention is limited only by the scope of the appended claims.

We claim:

1. A liquid varnish composition in an orally acceptable liquid vehicle means suitable for dental use and effective in combatting growth of caries-causing bacteria, said composition being capable of drying on teeth to yield at least initially a translucent, transparent or tooth colored film and capable of adherence to the dental infection site, said composition comprising an effective amount of at least one dentally acceptable antimicrobial means effective against *Streptococcus mutans* and an amount of benzoin effective to form said film and sufficient to permit effective communication of said antimicrobial means with the infection site and sustained release thereof when the composition is applied thereto.

2. The composition of claim 1 wherein the liquid vehicle means is ethanol.

3. The composition of claim 1 wherein the weight ratio of benzoin to antimicrobial means is in the approximate range of 10:1 to 1:10.

4. The composition of claim 1 including a plurality of antimicrobial means effective against *Streptococcus mutans*.

5. A liquid dental varnish composition suitable for painting onto teeth to combat oral infection by caries-causing bacteria, said composition consisting essentially of:

an orally acceptable liquid vehicle;
benzoin;
and an effective amount of at least one dentally acceptable antimicrobial means effective against *Streptococcus mutans* compatible with the liquid vehicle and the benzoin;
the liquid vehicle and the benzoin being present in suitable amounts such that the composition is capable of drying to form a solid transparent, translucent or tooth coloured coating on teeth to which the composition is applied and releasing at least one of said antimicrobial means over a sustained period of time into contact with infective sites on said teeth.

6. A two component liquid dental varnish composition-containing kit, the ingredients of which are collectively capable of combatting growth of caries-causing bacteria indigenous to the oral cavity, the kit comprising, in a first component, an effective amount of at least one dentally acceptable antimicrobial means effective against *Streptococcus mutans* in admixture with an amount of benzoin in an orally acceptable liquid vehicle means which is sufficient to permit effective communication of said antimicrobial means with a target site to which said first component may be applied, and to permit sustained release of said antimicrobial agent to said target site, and in a second distinct and separate component, an amount of a dentally acceptable, ethanol insoluble biodegradable polymeric sealant means in an orally acceptable liquid vehicle means, which is effective to seal the antimicrobial means and binder means ingredients of said first component in position over the target site.

7. A two component liquid dental varnish composition containing kit the ingredients of which are collectively capable of combatting growth of caries-causing bacteria indigenous to the oral cavity by painting onto an application site therein, the kit comprising:

a first component comprising in admixture an effective amount of at least one dentally acceptable antimicrobial means effective against *Streptococcus mutans*, an amount of benzoin which is effective in admixture with the antimicrobial means and an effective amount of an orally acceptable liquid vehicle means to form a film over the application site and to permit effective communication and sustained release of said antimicrobial means to the area onto which it is applied and, a second distinct and separate component compatible with said first component, comprising a sealing composition comprising a biodegradable polyurethane which in an amount sufficient, in admixture with an orally acceptable liquid vehicle means, when applied over the first component, to seal the first component in position over the target site.

8. The two component kit of claim 7 wherein the dentally acceptable antimicrobial means effective against *Streptococcus mutans* is selected from erythromycin, chlorhexidine, salts thereof and mixtures thereof.

9. The two component kit of claim 8 wherein said second component is a polyurethane varnish comprising an orally acceptable film-forming biodegradable polyurethane in a solvent selected from methylene chloride, ethanol, tri- and tetra-halogenated methanes, fully halogenated ethanes, and mixtures thereof.

10. The two component kit of claim 9 wherein said second component is an orally acceptable film forming biodegradable polyurethane in solution in methylene chloride.

11. The two component kit of claim 10 wherein the orally acceptable liquid vehicle means in the first component is ethanol.

* * * * *

UNITED STATES PATENT AND TRADEMARK OFFICE
CERTIFICATE OF CORRECTION

PATENT NO. : 4,883,534
DATED : November 28, 1989
INVENTOR(S) : H. J. Sandham, et al.

It is certified that error appears in the above-identified patent and that said Letters Patent is hereby corrected as shown below:

Title Page:

" [73] Assignee: University of Toronto Innovations Foundations, Toronto, Ontario, Canada"

should read

-- [73] Assignee: University of Toronto Innovations Foundation, Toronto, Ontario, Canada --.

Column 3, line 8, "appropiate" should read -- appropriate --.

Column 5, line 7, "inflitrate" should read -- infiltrate --.

Column 8, line 49, Example 6, second column, after "polyurethane varnish in", insert -- methylene chloride --.

Column 14, line 32, delete "which".

Signed and Sealed this

Eighth Day of October, 1991

*Attest:*

HARRY F. MANBECK, JR.

*Attesting Officer*         *Commissioner of Patents and Trademarks*